United States Patent [19]

Glisson et al.

[11] Patent Number: 4,999,191

[45] Date of Patent: Mar. 12, 1991

[54] *PASTEURELLA MULTOCIDA* VACCINE

[75] Inventors: John R. Glisson, Athens, Ga.; Charles L. Hofacre, Monroe, N.C.

[73] Assignee: University of Georgia Research Foundation, Inc., Athens, Ga.

[21] Appl. No.: 190,533

[22] Filed: May 5, 1988

[51] Int. Cl.[5] .......................... A61K 39/02; C12N 15/00
[52] U.S. Cl. ........................................ 424/92; 424/88; 424/93; 435/172.1
[58] Field of Search ............................ 424/92, 88, 93; 435/172

[56] References Cited

U.S. PATENT DOCUMENTS

| | | |
|---|---|---|
| 3,501,770 | 3/1970 | Gale et al. |
| 3,526,696 | 9/1970 | Gale et al. |
| 3,798,320 | 3/1974 | Weiss et al. |
| 3,853,990 | 12/1974 | Madigan et al. |
| 3,855,408 | 12/1974 | Maheswaran |
| 4,136,169 | 1/1979 | Rebers et al. |
| 4,167,560 | 9/1979 | Wohler, Jr. |
| 4,169,886 | 10/1979 | Hertman et al. ...................... 424/92 |
| 4,293,545 | 10/1981 | Kucera |
| 4,328,210 | 5/1982 | Kucera |
| 4,335,106 | 6/1982 | Kucera |
| 4,388,299 | 6/1983 | Kucera |
| 4,506,017 | 3/1985 | Kucrea |

*Primary Examiner*—Howard E. Schain
*Assistant Examiner*—Abdel A. Mohamed
*Attorney, Agent, or Firm*—Kilpatrick & Cody

[57] ABSTRACT

Mutogenesis of the Clemson University (CU) vaccine strain of *P. multocida* with N-methyl-N-nitro-N-nitrosoguanidine resulted in temperature sensitive (TS) mutants which grew at 37° C. but not 42° C. Two mutants, PM#1 and PM#3, were found to provide turkeys with a level of protection against challenge with a virulent serotype 3 *P. multocida* strain (P-1059) comparable to the protection provided by the CU strain. Intravenous (IV) inoculation of PM#1, PM#3, and CU was used to determine differences in virulence. PM#1 and PM#3 resulted in lower mortality and lameness than the CU strain. Histopathological evaluation of spleens at 24, 48, and 72 hours post IV inoculation demonstrated that the CU strain induced 2 times more splenic necrosis than either PM#1 or PM#3.

10 Claims, No Drawings

PASTEURELLA MULTOCIDA VACCINE

BACKGROUND OF THE INVENTION

This invention relates to modified strains of *Pasteurella multocida* for use in poultry vaccines.

It has been more than 100 years since the first fowl cholera vaccine was developed by Pasteur. Since then there have been many attempts at producing both live and inactivated fowl cholera vaccines. Bacterins have been found to induce immunity only to homologous serotypes while avirulent live vaccines provide protection to heterologous serotypes. Since there are many different serotypes of *Pasteurella multocida* that can lead to fowl cholera in turkeys it would appear to be more advantageous to vaccinate with a live vaccine.

There have been many live fowl cholera vaccines developed since Pasteur. The first successful avirulent live vaccine was the Clemson University strain (CU strain). The CU strain was found to provide both humoral and cell-mediated systemic immunity and protection to the major types of *P. multocida* infecting turkeys. Although the CU strain stimulates a good immune response in turkeys, it has the disadvantage of resulting in mortality as high as 4% following vaccination.

A number of subsequent *Pasteurella multocida* strains have been developed, for example, as described in U.S. Pat. Nos. 4,506,017, 4,388,299, 4,335,106, 4,328,210, 4,293,545, (bovine, porcine and ovine), U.S. Pat. Nos. 3,501,770, 3,526,696 (multi-bacterial vaccines to prevent shipping fever), U.S. Pat. No. 4,136,169 (poultry vaccine made from bacterins), and U.S. Pat. Nos. 4,169,886, 3,855,408 (attenuated poultry vaccines). There remains a need for a safe, effective vaccine providing good humoral and cell-mediated systemic immunity and protection to the major types of *P. multocida*.

It is therefore an object of the present invention to provide a live *P. multocida* vaccine for use in immunizing poulty.

It is a further object of the present invention to provide a live *P. multocida* strain that is an effective immunizing agent but less virulent than the Clemson University strain.

SUMMARY OF THE INVENTION

Mutogenesis of the Clemson University (CU) vaccine strain of *P. multocida* with N-methyl-N-nitro-N-nitrosoguanidine resulted in temperature sensitive (TS) mutants which grew at 37° C. but not 42° C. Seven TS mutants were evaluated for immunogenicity in turkeys. From these seven only two, PM#1 and PM#3, deposited with the ATCC on Apr. 19, 1988 and assigned ATCC Nos. 53766 and 53767, respectively, were found to provide turkeys with a level of protection against challenge with a virulent serotype 3 *P. multocida* strain (P-1059) comparable to the protection provided by the CU strain.

Intravenous (IV) inoculation of PM#1, PM#3, and CU was used as a method to determine differences in virulence. PM#1 and PM#3 resulted in lower mortality and lameness than the CU strain. Histopathological evaluation of spleens at 24, 48, and 72 hours post IV inoculation demonstrated that the CU strain induced two times more splenic necrosis than either PM#1 or PM#3.

DETAILED DESCRIPTION OF THE INVENTION

Two avirulent strains of *P. multicocida* have been developed for use as vaccines in poultry, especially turkeys. These strains, designated PM#1 and PM#3, were deposited with the American Type Culture Collection, Rockville, Md., on Apr. 19, 1988 and designated ATCC numbers 53766 and 53767, respectively.

These strains are lactose negative Gram negative rods that grow on blood agar but not McConkey agar and have the following characteristics shown on Table 1.

TABLE 1

| strain | Enzymes | | Carbohydrate Fermentation | | | | | Antibiotic Sensitivity | | | | | | Hemolysis | Plasmids |
| --- | --- | --- | --- | --- | --- | --- | --- | --- | --- | --- | --- | --- | --- | --- | --- |
| | Trp | Chy | Gln | Sor | Ara | Fuc | Gly | Tre | G | RA | B | S | TE | NA | | |
| PM 1 | − | − | + | + | − | − | − | − | I | R | I | s | s | s | wk | 0 |
| PM 3 | − | + | + | + | − | + | − | − | R | R | s | l | s | s | — | 0 |

Carbohydrate Fermentation
Gln = gluconate
Sor = L-sorbose
Ara = D-arabinose
Fuc = L-fucose
Gly = glycerol
Tre = trehalose Enzymes
Trp = trypsin
Chy = chymotrypsin Antibiotic Sensitivity
G = sulfisoxazole
RA = rifampin
B = bacitracin
S = streptomycin
TE = tetracycline
NA = nalidixic acid
R = resistant
I = intermediate
s = sensitive Hemolysis
wk = weak These strains have been demonstrated to be as effective as the widely used Clemson University strain of *P. multicocida*, but have the advantage that they cause less pathological damage, as determined by histological examination.

The vaccines can be administered using methods known to those skilled in the art, including by aerosol, by os, or injection. The preferred method of vaccination in turkeys is by innoculating drinking water with PF#1 at a concentration of $5 \times 10^8$ CFU/bird or with PM#3 at a concentration of $5 \times 10^9$ CFU/bird.

PRODUCTION OF MUTANTS

The Clemson University strain of *P. multicocida* was first reported in *Poultry Science* 47, 1162 (1968). It is a naturally occuring strain of low virulence (mortality of up to 2%), stable, and effective in the immunization of turkeys. One ml of a 1 mg/ml solution N-methyl-N-nitro-N-nitrosoguanidine (NTG) in physiological saline (PSS) was added to 5 ml of a 9 hour broth culture of the CU strain grown in brain heart infusion broth (BHI).

The culture was incubated at 37° C. for 30 minutes with constant agitation. The cells were then washed by centrifugation at 5000× G for 15 minutes, the supernatant removed and the pellet resuspended in 5 ml of PSS. This procedure was performed three times with the final pellet being suspended in 1 ml PSS. Ten fold dilutions were then made of the suspension and 0.1 ml of each dilution was placed onto dextrose starch agar (DSA) plates, which were incubated (non-inverted) at 30° C. After 72 hours three replicas of all plates with colonies were made onto DSA plates using a sterile velvet cloth held tightly over an aluminum cylinder. These replica plates were incubated at 30° C., 37° C., and 42° C. for 24 hours. Colonies growing at 30° C. and 37° C. but not at 42° C. were considered to be temperature sensitive (TS).

42 temperature sensitive mutants were isolated following NTG mutagenesis procedures. From these 42 isolates, 7 were selected for immunogenicity studies. This selection was based on an individual isolate's ability to grow on blood agar and in BHI. Many of the isolates grew very poorly and were not considered good candidates for further study. When experiments were performed to evaluate immunogenicity of the 7 chosen mutants, several of those were grown at temperatures other than 37° C. to enhance their growth. The growth of those isolates, M#5 B, M#5 G, and M6-18, was more adversely affected by incubation at temperatures of 37° C. or higher than was the growth of the other 4 isolates selected for further study.

Challenge Technique

The challenge technique, which utilizes uniform numbers of organisms administered by a natural route, was used for both vaccinations and challenges. One drop of *P. multocida* grown in BHI was placed into one eye, a drop was placed into one nostril, and 2 ml was squirted into the palatine cleft using a curved blunted cannula.

Turkeys and Facilities

All turkeys used in this study were broad breasted white turkeys from a commercial turkey hatchery. The birds were grown from 1 day of age until the time of vaccination in an isolated curtain-sided barn in floor pens on softwood litter.

At the time of vaccination all birds were moved to another curtain-sided barn and placed in floor pens on softwood litter with at least 20 feet separating the different treatment groups. The caretaker (wearing clean boots and coveralls) entered only one treatment pen each day to prevent cross-contamination.

At the time of challenge all birds were moved to another curtain-sided barn and placed in floor pens on softwood litter.

Evaluation of Mutants

Studies were conducted to evaluate the relative immunogenicity of the TS mutants.

Study 1

Thirty 7-week-old straight run turkeys were divided into 3 treatment groups of 10 each. One group was inoculated with a 15 hour BHI broth culture ($2.0\times10^9$ CFU/ml) of mutant M#5 B, grown at 30° C. The second group was inoculated with a 15 hour BHI broth culture ($2.0\times10^9$ CFU/ml) of the CU strain grown at 37° C. The third group was uninoculated control birds. Inoculation was by the oculo-naso-oral method described above.

All three treatment groups were challenged 3 weeks post vaccination with a virulent serotype 3(P-1059) *P. multocida*. The challenge organism was grown for 15 hours at 37° C. in BHI broth and had bacterial count of $2.5\times10^9$ CFU/ml.

Study 2

Sixty 7-week-old straight run turkeys were divided into 4 treatment groups of 15 each. One group was inoculated with a 15 hour BHI broth culture ($3.0\times10^9$ CFU/ml) of mutant M#5G, grown at 25° C. The second group was inoculated with a 15 hour BHI broth culture ($1.0\times10^9$ CFU/ml) of mutant M6-18, grown at 30° C. The third group was inoculated with a 15 hour BHI broth culture ($1.0\times10^9$ CFU/ml) of the CU strain, grown at 37° C. The fourth group was uninoculated controls.

All four treatment groups were challenged 3 weeks post vaccination with a virulent serotype 3(P-1059) *P. multocida*. The challenge organism was grown for 15 hours at 37° C. in BHI broth and had bacterial count of $3.0\times10^8$ CFU/ml.

Study 3

Fifty 12-week-old straight run turkeys were divided into 5 treatment groups of 10 each. One group was inoculated with a 15 hour BHI broth culture ($2.0\times10^9$ CFU/ml) of mutant PM#1, grown at 37° C. The second group was inoculated with a 15 hour BHI broth culture ($4.0\times10^7$ CFU/ml) of mutant PM#2, grown at 37° C. The third group was inoculated with a 15 hour BHI broth culture ($1.0\times10^7$ CFU/ml) of mutant PM#3, grown at 37° C. The fourth group was inoculated with a 15 hour BHI broth culture ($5.0\times10^7$ CFU/ml) of mutant PM#4, grown at 37° C. The fifth group was uninoculated control birds.

All five treatment groups were challenged 3 weeks post vaccination with a virulent serotype 3(P-1059) *P. multocida*. The challenge organism was grown for 15 hours at 37° C. in BHI broth and had bacterial count of $4.0\times10^8$ CFU/ml).

DETERMINATION OF VIRULENCE

Study 1

Twenty-four 9-week-old turkeys were divided into 3 groups of 8 turkeys and injected intravenously (IV) with 1 ml of either $5\times10^8$, $5\times10^7$ or $5\times10^6$ CFU/ml of a 19 hour BHI broth culture of the CU strain. Twenty-four 8-week-old turkeys were divided into 3 groups of 8 each and injected with 1 ml IV of either $2\times10^8$, $2\times10^7$, or $2\times10^6$ CFU/ml of a 19 hour BHI broth culture of the mutant PM#1. Thirty-six 10-week-old turkeys were divided into 3 groups of 12 turkeys each and injected with 1 ml IV of either $1\times10^7$, $1\times10^6$, or $1\times10^5$ CFU/ml of a 19 hour BHI broth culture of the mutant PM#3. Fifteen 10-week-old turkeys were inoculated IV with 1 ml PSS.

Mortality was recorded daily and after 10 days survivors were evaluated for incidence of lameness. The hock and stifle joints of lame birds were opened and samples of joint fluid taken by sterile swab. The swabs were inoculated onto blood agar plates. Birds were only considered lame if both clinically lame and *P. multocida* was isolated from the joints.

Study 2

One hundred twenty 10-week-old straight run turkeys were divided into 4 groups of 30 each. All birds in the 4 treatment groups were injected IV with 1 ml of $2 \times 10^6$ CFU/ml of either PM#1, PM#3, the CU strain or sterile PBS. The bacteria were grown for 19 hours in BHI broth and then diluted with PBS.

At 24, 48, and 72 hours post inoculation 5 birds were removed from each treatment group. The spleen and left lung were removed and placed immediately into 10% buffered formalin. Tissues were then evaluated by light microscopy. The lungs were evaluated for fibrin, interstitial pneumonia and necrosis. The spleens were evaluated for hyperplasia and necrosis. The histological evaluation was based on a 1 to 4 rating with a rating of 1=normal, 2=focal lesion, 3=multifocal lesions and 4=diffuse lesions.

Mortality was recorded daily and after 10 days survivors were evaluated for the incidence of lameness. The hock and stifle joints of lame birds were opened and sampled with sterile swabs and the swabs were inoculated onto blood agar plates. Birds were only considered lame if both clinically lame and P. multocida was isolated from the joints.

SELECTION OF MUTANTS

Study 1

The nonvaccinated control turkeys had no survivors following challenge. The birds vaccinated with the mutant M#5B had 10% survival while the CU strain resulted in 60% survival after challenge.

Study 2

The nonvaccinated control turkeys had no survivors following challenge. The turkeys vaccinated with the mutant M6-18 had 15% survival while the turkeys vaccinated with the mutant M#5G had only 5% survival. The CU strain vaccinated turkeys had 90% survival following challenge.

Study 3

The nonvaccinated control turkeys had no survivors following challenge. Mutant PM#3 provided the greatest amount of protection with 73% of the turkeys surviving challenge. There was 60% survival among the turkeys vaccinated with Pasteurella mutant PM#1. Pasteurella mutants PM#2 and PM#4 gave much lower survival at 30% and 0% respectively.

DETERMINATION OF VIRULENCE

Study 1

As shown in Table 2, mutants PM#1 and PM#3 appeared to be less virulent than the CU strain. At all dilution levels PM#1 and PM#3 resulted in less total birds affected following intravenous inoculation of the organism.

The $10^6$ CFU/ml dose was chosen for the histological IV pathogenicity evaluation because at this dosage the CU strain caused considerable mortality and lameness while PM#1 and PM#3 did not.

Study 2

Ten days post challenge inoculation of the CU strain resulted in 1 dead and 3 lame birds. Inoculation of PM#1 resulted in 1 dead and 3 lame and PM#3 resulted in 1 dead and 1 lame.

There were no differences in any of the treatment groups in hisological evaluation of the lungs. There were also no differences found in splenic hyperplasia between treatments as seen in Table 3. There were differences in pyogranulomatous necrosis of the spleens (Table 4) with CU inoculated birds having mean lesion scores of 2.6, 2.4, and 2.4 at 24, 48, and 72 hours post inoculation. The turkeys inoculated with PM#1 had mean lesion scores of 1.0, 14 and 1.0 at 24, 48, and 72 hours respectively. This difference was also quite evident grossly at necropsy as the CU inoculated turkeys had enlarged spleens with multifocal pale areas which was not seen in the PM#1 and PM#3 inoculated turkeys.

The two mutant strains of *P. multicocida* that provided turkeys with the most protection from a challenge with a highly virulent serotype 3 strain of *P. multocida* (P-1059) were PM#1 and PM#3.

It is very difficult to exhibit clear-cut differences in virulence between organisms of low virulence. Simply giving low virulence organisms by natural routes will not distinguish differences in virulence, therefore, an abnormal method such as IV inoculation must be used to determine if any differences in virulence exist. Using intravenous inoculation as a method to determine virulence, mutants PM#1 and PM#3 were found to be less virulent than the CU strain resulting in less mortality and less lameness. Of the parameters examined histopathologically, only splenic necrosis was found to be of value in determining virulence. The CU strain resulted in nearly 2 times more splenic necrosis at all 3 sampling times than did PM#1 and PM#3.

The oculo-nasal-oral inoculation technique was developed for thse preliminary studies to insure that every bird received a consistent dose of vaccine and a consistent challenge dose. Another advantage to this technique was that it employed natural routes of entry of *P. multocida* into turkeys.

TABLE 2

Determination of Intravenous Virulence Dose.

| Vaccine | CFU/ML | % Mortality | % Lame | Total % Effected[b] |
|---|---|---|---|---|
| PM#1 | $2\times10^8$ | 37.5 | 62.5 | 100 |
| | $2\times10^7$ | 12.5 | 12.5 | 25 |
| | $2\times10^6$ | 0 | 25 | 25 |
| PM#3 | $1\times10^7$ | 45.5 | 18 | 63.5 |
| | $1\times10^6$ | 15 | 8 | 23 |
| | $1\times10^5$ | 0 | 0 | 0 |
| CU STRAIN | $5\times10^8$ | 100 | NA | 100 |
| | $5\times10^7$ | 100 | NA | 100 |
| | $5\times10^6$ | 12.5 | 62.5 | 75 |
| CONTROL | PBS | 0 | 0 | |

[a]Percent of total number of turkeys which were lame but did not die.
[b]Total percent which were either lame or died.

TABLE 3

Histoloical determination of virulence by scoring of splenic hyperplasia.

| Time post inoculation (Hours) | Treatment Control | CU | PM#1 | PM#3 |
|---|---|---|---|---|
| 24 | 1.0 | 2.2 | 1.0 | 1.6 |
| 48 | 1.2 | 1.2 | 1.2 | 1.2 |
| 72 | 1.2 | 1.2 | 1.8 | 1.8 |

Scoring system:
1 = Normal
2 = Focal lesion
3 = Multifocal lesion
4 = Diffuse lesions

TABLE 4

Histological determination of virulence by scoring of splenic pyogranulomatous necrosis.

| Time post inoculation (Hours) | Treatment | | | |
|---|---|---|---|---|
| | Control | CU | PM#1 | PM#3 |
| 24 | 1.0 | 2.6 | 1.2 | 1.0 |
| 48 | 1.0 | 2.4 | 1.2 | 1.4 |
| 72 | 1.0 | 2.4 | 1.8 | 1.0 |

Scoring system:
1 = Normal
2 = Focal lesion
3 = Multifocal lesion
4 = Diffuse lesions This data demonstrates the effectiveness and safety of vaccines made using either of two *Pasteurella multicocida* temperature sensitive mutants designated PM-1 and PM-3, deposited on Apr. 19, 1988 with the American Type Culture Collection, Rockville, Md. and assigned ATCC numbers PM1 53766 and PM3 53767, respectively. Both strains provided adequate protection against virulent challenge with serotype 3 (P-1059) *Pasteurella multicocida* while being less virulent.

Modifications and variations of the present invention, vaccines for poultry utilizing *Pasteurella multicocida* mutants deposited with the ATCC, or derivatives or mutants thereof, will be obvious to those skilled in the art from the foregoing detailed description. Such modifications and variations are intended to come within the scope of the appended claims.

We claim:

1. A vaccine for poultry against *Pasteurella multocida* comprising a mutated strain of *Pasteurella multocida*, PM#1, deposited with the American Type Culture Collection, Rockville, Md. on Apr. 19, 1988 and designated ATCC 53766, derived from the Clemson University strain and effective against serotype 3 *Pasteurella multocida*.

2. A vaccine for poultry against *Pasteurella multocida* comprising a mutated strain of *Pasteurella multocida*, PM#3, deposited with the American Type Culture Collection, Rockville, Md. on Apr. 19, 1988 and designated ATCC 53767, derived from the Clemson University strain and effective against serotype 3 *Pasteurella multocida*.

3. The vaccine of claim 1 in unit dosage form to provide between $10^7$ and $10^9$ CFU of *Pasteurella multocida* ATCC 53766 to a bird to be vaccinated.

4. The vaccine of claim 2 in unit dosage form to provide between $10^7$ and $10^9$ CFU of *Pasteurella multocida* ATCC 53767 to a bird to be vaccinated.

5. A method for immunizing poultry against infection with *Pasteurella multocida* comprising vaccinating the poultry with a mutated strain of *Pasteurella multocida*, PM#1, deposited with the American Type Culture Collection, Rockville, Md. on Apr. 19, 1988 and designated ATCC 53766, derived from the Clemson University strain and effective against serotype 3 *Pasteurella multocida*.

6. The method of claim 5 wherein the poultry is vaccinated with between $10^7$ and $10^9$ CFU of *Pasteurella multocida* ATCC 53766 per bird.

7. The method of claim 6 wherein the poultry is vaccinated with $5 \times 10^8$ CFU/bird.

8. A method for immunizing poultry against infection with *Pasteurella multocida* comprising vaccinating the poultry with a mutated strain of *Pasteurella multocida*, PM#3, deposited with the American Type Culture Collection, Rockville, Md. on Apr. 19, 1988 and designated ATCC 53767, derived from the Clemson University strain and effective against serotype 3 *Pasteurella multocida*.

9. The method of claim 8 wherein the poultry is vaccinated with between $10^7$ and $10^9$ CFU of *Pasteurella multocida* ATCC 53767 per bird.

10. The method of claim 9 wherein the poultry is vaccinated with $5 \times 10^8$ CFU/bird.

* * * * *